United States Patent
Halos et al.

(10) Patent No.: US 9,499,447 B2
(45) Date of Patent: Nov. 22, 2016

(54) STABLE ORGANIC-CARRIER-BASED MICROBIAL INOCULANTS AND CULTURES

(71) Applicants: Saturnina Halos, Laguna (PH); Ponciano Halos, Laguna (PH)

(72) Inventors: Saturnina Halos, Laguna (PH); Ponciano Halos, Laguna (PH)

(*) Notice: Subject to any disclaimer, the term of this patent is extended or adjusted under 35 U.S.C. 154(b) by 0 days.

(21) Appl. No.: 13/753,810

(22) Filed: Jan. 30, 2013

(65) Prior Publication Data

US 2013/0239633 A1 Sep. 19, 2013

Related U.S. Application Data

(63) Continuation of application No. 12/663,222, filed as application No. PCT/PH2007/000012 on Jun. 21, 2007, now abandoned.

(51) Int. Cl.
| | | |
|---|---|---|
| C12N 1/20 | (2006.01) | |
| C05F 11/08 | (2006.01) | |
| C12N 1/04 | (2006.01) | |

(52) U.S. Cl.
CPC .......... *C05F 11/08* (2013.01); *C12N 1/04* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 4,021,581 A | 5/1977 | Sing | |
| 5,919,695 A | 7/1999 | Vendamuthu et al. | |
| 6,008,027 A | 12/1999 | Langner | |
| 7,422,737 B1* | 9/2008 | Nussinovitch et al. | 424/93.4 |
| 2010/0178303 A1 | 7/2010 | Halos et al. | |

OTHER PUBLICATIONS

Nur et al. (Can. J. Microbiol., vol. 26(4) : 482-485 (1980)).*
Bashan et al. (Applied and Environ. Microbiol., 56(3) :769-775 (1990).*
Eckert et al. (International Journal of Systematic and Evolutionary Microbiology (2001), 51, 17-26).*
Reddy (Vegetable Research in India—An IIHR Perspective. In "Impact of Vegetable Research in India", Edited by Kumar et al., Proceedings 13, NCAP 2004. Printed at Chandu Press D-97, Shakarpur, New Delhi-110 092), pp. 44-58.*
Khammas et al., Res Microbiol. Nov.-Dec. 1989;140(9):679-93.*
Tarrand et al., Can J Microbiol. Aug. 1978;24(8):967-80.*
Fages et al., Appl Microbiol Biotechnol (1990) 32:473-478.*
Hartmann et al. The Prokaryotes. 2006, vol. 5, pp. 115-140.*
Desmons et al., Appl. Bioch. Biotech. 70 (1998) 513-526.*
International Search Report prepared by the United States Patent and Trademark Office on Oct. 8, 2008, for International Application No. PCT/PH07/00012.
Written Opinion of the International Searching Authority prepared by the United States Patent and Trademark Office on Oct. 8, 2008, for International Application No. PCT/PH07/00012.
Kang et al., "Production of Lyophilized Culture of *Lactobacillus acidophilus* with Preserving Cell Viability," Biotechnology and Bioprocess Engineering, 1999, vol. 4, Iss. 1, pp. 36-40.
Leland, "Environmental-Stress Tolerant Formulations of *Metarhizium anisopliae* var. acridum for Control of African Desert Locust (*Schistocerca gregaria*)," Ph.D. Dissertation, Virginia Polytechnic Institute and State University, 2001, 188 pages.
Schank et al., "Plant Yield and Nitrogen Content of a Digitgrass in Response to *Azospirillum* Inoculation," Applied and Environmental Microbiology, Feb. 1981, vol. 41, No. 2, pp. 342-345.
Official Action for U.S. Appl. No. 12/663,222 mailed May 25, 2012, 6 pages.
Official Action for U.S. Appl. No. 12/663,222 mailed Jul. 30, 2012, 7 pages.

* cited by examiner

*Primary Examiner* — Irene Marx
(74) *Attorney, Agent, or Firm* — Sheridan Ross P.C.

(57) ABSTRACT

The present invention relates to methods for producing microbial preparations for crop production and microbial preparations produced through such methods. The formulations contain microbial inoculants like *Azospirillum* spp. which are grown in a complex medium, lyophilized with powdered milk and further supplemented with minerals and vitamins, starch and inert substances such as talc, chalk and diatomaceous earth. The products manufactured by such methods have shelf-lives of more than 3 years. They are used to inoculate seeds, seedlings and planting materials among different agriculture and forestry species for enhancing root, root hair an shoot formation, enabling plants to efficiently use soil nutrients, supplying plants with nitrogen from the air, tolerating drought and protecting plants from root pathogenes.

6 Claims, No Drawings

STABLE ORGANIC-CARRIER-BASED MICROBIAL INOCULANTS AND CULTURES

CROSS REFERENCE TO RELATED APPLICATIONS

This application is a continuation application of U.S. application Ser. No. 12/663,222, filed Dec. 4, 2009, now abandoned, which is a national stage application under 35 U.S.C. 371 of PCT Application No. PCT/PH2007/000012 having an international filing date of 21 Jun. 2007, which designated the United States, the entire disclosures of which are hereby incorporated herein by reference.

FIELD OF INVENTION

The present invention relates to microbial preparations for crop production.

BACKGROUND ART

The present invention relates to microbial preparations for crop production, specifically microbial inoculants incorporated in carriers that provide protection for the colonizing microorganisms and the method for producing the same.

In theory, microbial inoculants, without human intervention, have a low survival rate and efficiency in their natural soil environment because of the insufficient colony forming units per gram soil. Since the 1950s, biofertilizers that have an increased colony increased inoculum potential concentration have been developed and commercialized. There are three basic types of biofertilizers: liquid-phase, suspension-or, solid carrier-based microbial inoculants. Commercial biofertilizers effectively enhance soil fertility because they contain sufficient cells of efficient strains of specific microorganisms, that can fix atmospheric nitrogen, solubilize/mineralize phosphorous and potash or decompose organic wastes and augment plant growth with hormones and other growth promoting substances with their biological activities.

The present invention is a carrier-based biofertilizer that promotes growth of plants of any type of terrestrial biome, using special biological inoculants, such as plant growth promoting rhizobacteria. The invention induces extensive root and root hair formation, enable plants to efficiently use soil nutrients, supply plants with nitrogen from the air, increase drought tolerance and protect the plants from pathogens. Further, the inoculants can be mixed with an insecticide or fungicide without any appreciable decrease in effectivity.

The closest prior art are reported in WO 2007/014974 ("Aseptic Mycorrhization Inoculant and In vitro and Ex vitro Application Methods"), WO 1994/006732 ("Method for Obtaining a Wettable Powder Inoculant for Use with Leguminous Crops"), WO 2006/070061 ("Stable Microbial Inoculants and Methods for Production of Them"), WO 2002/015702 ("A Thermo-stable Bio-matrix"), and WO 2000/034440 ("Microorganisms for Improving Plant Productivity").

According to WO 2007/014974 ("Aseptic Mycorrhization Inoculant and In vitro and Ex vitro Application Methods"), a low-viscosity, light, semi-solid agar-type base culture medium is used to facilitate the penetration of the root in the inoculant, as well as to potentiate and preserve the infectiousness of arbuscular mycorrhizal fungi, such as those of the present invention. WO 2007/014974 sought to obtain the advantage of being as effective in in vitro as well as ex vitro inoculation by using a semi-solid inoculant. However, it is gel-based and has a short shelf-life, which the present invention seeks to address.

WO 1994/006732 ("Method for Obtaining a Wettable Powder Inoculant for Use with Leguminous Crops") reports a method for obtaining a wettable powder inoculant formulation for use with leguminous crops, comprising the industrialization of an inoculants for leguminous from a centrifugated biological mass of *Rhizobium* spp twice immersed in a cryogenic protective solution rich in sugar and protein which is subjected to a lyophilization method. Like the present invention, it is formulated with substances rich in polysaccharides and associated with a cellular protector which substitutes the previously used peat support. It also has a long shelf life of up to 25 months even when stored at room temperature. However, WO 1994/006732 can only be used for leguminous crops. Further, the formulation of the carrier uses sugar and protein while the present invention uses milk and glycerin. Also, WO 1994/006732 does not teach that the powder inoculant with a pest protectant such as an insecticide.

WO 2006/070061 ("Stable Microbial Inoculants and Methods for Production of Them") teaches away from the present invention. It describes water containing microbial inoculants in paste form with shelf life of at least 3 months, preferably 12 months. It reports that drying, which is a method utilized in the present invention is complicated, expensive and may even be impossible.

WO 2002/015702 ("A Thermo-stable Bio-matrix") reports a method for producing a thermo-stable biodegradable medium for storage of biological materials wherein the biological material includes: a pesticide; a viricide; a bactericide; a fungicide; and a combination of these. While the method is similar in that the biological material can be safely mixed with potentially degradative substances such as pesticides, viricides, bactericides, fungicides or a combination of these, the medium is structurally different because it is gel-based and contains a biopolymer selected from the group of xanthan gum, acacia gum, guar gum, gellan, starch or a combination thereof, unlike the present invention which is in powder form. Thus, it is no surprise that WO 2002/015702 discloses a maximum shelf life of only eighteen (18) months, which is considerably shorter than that of the present invention which allows storage of at least three (3) years.

WO 2000/034440 ("Microorganisms for Improving Plant Productivity") is directed to microbes which includes the microorganism *Azospirillum brasilense*, which belongs to the same genus as some of those in the present invention. As with the present invention, two specific strains of microbial inoculant of WO 2000/034440 is effective for increasing the productivity of both nonlegume and legume plants as well as vegetable plants over a wide variety of soil types and climates. However, the WO 2000/034440 is narrowly directed only to the *Azospirillum brasilense*, a microorganism not covered by the present application. Further, it does not teach an inventive carrier nor the method of production that prolongs its shelf life.

The present invention, the microbes, method and product, are absolutely different and improve over other known methods and products and have considerable advantages over the nature and quality of the methods and products, particularly in the storage life of the microbial preparation.

DISCLOSURE OF THE INVENTION

The present invention relates to microbial preparations for crop production such as seed, seedling and other planting material inoculants have been the subject of many researches in the past 25 years in the Philippines. They have been shown to be useful in increasing and protecting crop yields. However, they have not been put into commercial production because of their short shelf-lives which limit their effective distribution. This is also true of microbial inoculants for processing foods. Prior art discloses a shelf life of a maximum of only eighteen (18) months. This invention is intended to solve this problem of short shelf-lives and allow for the viable commercialization of microbial inoculants. The invention is expected to produce products with a huge market since biochemical catalysts including microbial preparations have agricultural, food and forestry applications.

The invention covers dried, semi-solid and related formulations of microbial inoculants like *Azospirillum* spp. and *Bacillus pumilus*. These bacteria are used to inoculate seeds and seedlings of different agriculture and forestry species to promote among others, the extensive root and root hair formation, enable plants to efficiently use soil nutrients, supply plants with nitrogen from the air, increase drought tolerance and protect the plants from root pathogens. These formulations are prepared in the following manner:

The microbes such as *Azospirillum* spp. And *Bacillus pumilus* are grown in fermentors using special media which contain substrates including high protein feed ingredients such as fish meal/bone meal/blood meal/soya meal, table sugar and tablet salt at 30° C. The bacterial cells are harvested by methods like filtration or centrifugation, added with powdered milk/glycerol to wet the cells and the *Azospirillum* mixture lyophilized. The products are formulated under sterile conditions with different proportions of components like the bacterial preparations, minerals, milk, vitamins and flour with or without talc/chalk/diatomaceous earth using standard mechanical devices. The dried and semi-solid products are packed or the tablets are made usually under sterile conditions.

The products as invented have extended the shelf-lives of the biochemical catalysts/microbial preparations by at least 3 years way beyond the 3 months observed with the non-lyophilized or other inoculants now available in very limited amounts in the market. The special media used to grow the bacteria improve the tolerance of the bacteria to lyophilization. Milk not only improves the tolerance of the bacteria to lyophilization; it also provides some vitamins, carbohydrates and minerals for a good start of the bacteria with inoculated plants. *Bacillus pumilus* need not be lyophilized because it is a spore former and can resist adverse conditions for many years. The added vitamins, minerals, flour and talc/chalk/diatomaceous earth also provide additional nutrients to selectively enrich the growth of the desired bacteria and the inoculated plants in problem soils with limiting micronutrients.

Characteristics of the Microorganisms

*Azospirillum* is made up of curved rod cells, 1 mm in diameter with varying sizes and shapes. It can have polar and peritrichous flagella and undergoes encystment. Its pinkish, whitish orange colonies vary in shape and surface characteristics. Carbon sources include organic acids and sugars. The nitrogen sources are amino acids, $N_2$, $NH_4^+$ and $NO_3$. Respiration can be aerobic, microaerophilic or anaerobic. It is capable of aerotaxis, chemotaxis and can form clumps.

*Bacillus pumilus* consists of rod-shaped cells, which can form endospores that are very resistant to many adverse conditions. Sporulation is not repressed by exposure to air. It is gram positive, or positive only in the early stages of growth, or negative. The flagellation is peritrichous or degenerately peritrichous. It can be aerobic or facultatively anaerobic. Oxygen is the terminal electron acceptor. Colony morphology and size are very variable on some media. It exhibits a wide diversity of physiological ability; psychrophilic to thermophilic; acidophilic to alkaliphilic. Some strains are salt tolerant while others have a specific requirement for salts. Catalase is formed but may be oxidase positive or negative. It requires biotin and some strains also require amino acids. Spores formed occur ubiquitously. The mole % G+C of the DNA ranges from 39.0-46.9 for 37 strains DNA-DNA hybridization studies indicate that the species is genetically homogenous.

The depository institution for these isolates is the UP-NSRI Culture Collection at Diliman, Quezon City. File numbers of some culture deposits are stated below while others will be submitted when already available.

*Azospirillum halopraeferens*—UPCC 1370
*Azospirillum lipoferum*—UPCC 1371
*Bacillus pumilus*—UPCC 1372
*Azospirillum* SC/PH—UPCC 1373
*Azospirillum* AH/EH—UPCC 1374

In addition, isolates *Azospirillum* SC/PH (UPCC 1373) and *Azospirillum* AH/EH (UPCC 1374) were deposited with the Agriculture Research Culture Collection (NRRL) International Depositary Authority, 1815 N. University Street Peoria, Ill. 61604 USA on Sep. 15, 2009. The NRRL Accession numbers are NRRL B-50317 for *Azospirillum* SC/PH (UPCC 1373) and NRRL B-50318 for *Azospirillum* AH/EH (UPCC 1374). It is averred that the deposited material has been accepted for deposit under the Budapest Treaty on the International Recognition of the Deposit of Microorganisms for the purpose of Patent Procedure and that all restrictions on the availability to the public of the material so deposited will be irrevocably removed upon granting of a patent, and the deposit is intended to meet all of the requirements of 37 C.F.R. 1.801-1.809. The deposits will be maintained in the depository for a period of thirty years, or five years after the last request, or for the enforceable life of the patent, whichever is longer, and will be replaced as necessary during that period.

Shelf Life

Extensive literature attests that such dried dormant microbial cells can remain viable for years. To further protect the product from environmental assault, nutrients that serve as buffer against changes in temperature and other environmental shock as well as provide the initial growth factors for the microbes to grow once the product gets wet and the cells start metabolizing. However, the product is vulnerable to fungal growth and/or grain beetles which considerably shorten its shelf life. Experiments were then conducted to test the inclusion in the product of fungicides and insecticides.

Two commercial fungicidal preparations and two insecticidal preparations (organic and synthetic) were added to the microbial preparation following manufacturer's recommended dosages. Liquid organic pesticides were absorbed in flour and added to the microbial preparation. These products were kept in storage for 6 months-3 years.

All products added with fungicides and insecticides did not show any infection nor infestation within the 3 years that these were kept in storage. All products tested showed the expected effect of a viable, healthy microbe: reduced inorganic fertilizer requirement in all the crops tested (rice, corn, pepper, onions, garlic, et. al), protection from bacterial leaf blight infection in rice and fungal root rot in onion, early maturity in rice, robustness and greenness of treated crops.

In an alternative embodiment, a pesticide, a viricide, a bactericide, a fungicide, or a combination of these may be added to the microbial inoculant to further prolong its shelf life.

Protection is being sought for preparation of biochemical catalysts/biofertilizers characterized by the 1) addition of vitamins and minerals among others, 2) harvesting by methods including centrifugation/filtration, and 3) lyophilization accompanied by skim milk with myo-inositol or glycerol or b) skim milk with honey, 4) the mixing of plant growth promoting rhizobacteria like *Azospirillum halopraeferens, Azospirillum lipoferum, Azospirillum* SC/PH or *Azospirillum* AH/EH cells with carriers like sugar, flour, talc/chalk/diatomaceous earth 5) an insecticide, a viricide, a fungicide, or a combination of these and 6) in powder, semi-solid, liquid or other forms, the products have extended shelf-lives of more than 3 years. These innovations make these products different from other formulations. They can induce changes like extensive root proliferation, drought tolerance, increased crop growth, yield and farmers' net incomes, beside being environment-friendly.

The invention claimed is:

1. A microbial inoculant consisting of a lyophilized bacterial microorganism selected from the group consisting of *Azospirillum* SC/PH having NRRL accession number B-50317, and *Azospirillum* AH/EH having NRRL accession number B-50318, wherein the microbial inoculant is produced by the steps of:
   a. growing a microbial colony from a culture of *Azospirillum* SC/PH having NRRL accession number B-50317 or *Azospirillum* AH/EH having NRRL accession number B-50318 at 30° C. in an organic medium comprising a mixture of high protein and vitamin-supplemented feed formula, wherein the high protein feed formula consists essentially of fish meal, bone meal, blood meal, or soya meal and table sugar and table salt;
   b. harvesting microbial cells from the medium;
   c. mixing the harvested microbial cells from step (b) with milk and glycerol prior to the step of lyophilization;
   d. drying the harvested cells from step (c) by lyophilization;
   e. grinding the dried cells into powder; and
   f. mixing the power with nutrients selected from the group consisting of vitamins, minerals, flour, talc, chalk, diatomaceous earth and combinations thereof;

and wherein the inoculant has a shelf-life of about 3 years.

2. The microbial inoculant of claim 1, wherein the lyophilized bacterial microorganism is *Azospirillum* SC/PH, having NRRL accession number B-50317.

3. A biofertilizer comprising a microbial inoculant consisting of a lyophilized bacterial microorganism selected from the group consisting of *Azospirillum* SC/PH having NRRL accession number B-50317, and *Azospirillum* AH/EH having NRRL accession number B-50318, and a component selected from the group consisting of a pesticide, a viricide, a bactericide, a fungicide and combination thereof, wherein the microbial inoculant is produced by the steps of:
   a. growing a microbial colony from a culture of *Azospirillum* SC/PH having NRRL accession number B-50317 or *Azospirillum* AH/EH having NRRL accession number B-50318 at 30° C. in an organic medium comprising a mixture of high protein and vitamin-supplemented feed formula, wherein the high protein feed formula consists essentially of fish meal, bone meal, blood meal, or soya meal and table sugar and table salt;
   b. harvesting microbial cells from the medium;
   c. mixing the harvested microbial cells from step b with milk and glycerol prior to the step of lyophilization;
   d. drying the harvested cells from step (c) by lyophilization;
   e. grinding the dried cells into powder; and
   f. mixing the power with nutrients selected from the group consisting of vitamins, minerals, flour, talc, chalk, diatomaceous earth and combinations thereof;

and wherein the inoculant has a shelf-life of about 3 years.

4. The microbial inoculant of claim 1, wherein the lyophilized bacterial microorganism is *Azospirillum* AH/EH having NRRL accession number B-50318.

5. The biofertilizer of claim 3, wherein the lyophilized bacterial microorganism is *Azospirillum* SC/PH, having NRRL accession number B-50317.

6. The biofertilizer of claim 3, wherein the lyophilized bacterial microorganism is *Azospirillum* AH/EH having NRRL accession number B-50318.

* * * * *